(12) United States Patent
Kang et al.

(10) Patent No.: US 9,228,075 B2
(45) Date of Patent: *Jan. 5, 2016

(54) COMPOSITION AND METHOD FOR INHIBITING GAS HYDRATE FORMATION

(75) Inventors: Seong-Pil Kang, Daejeon (KR); Dongwook Lee, Daejeon (KR); Howon Ra, Daejeon (KR); Kisub Kim, Seoul (KR)

(73) Assignee: Korea Institute of Energy Research, Daejeon (KR)

( * ) Notice: Subject to any disclaimer, the term of this patent is extended or adjusted under 35 U.S.C. 154(b) by 704 days.

This patent is subject to a terminal disclaimer.

(21) Appl. No.: 13/463,199

(22) Filed: May 3, 2012

(65) Prior Publication Data

US 2013/0112923 A1 May 9, 2013

(30) Foreign Application Priority Data

Nov. 3, 2011 (KR) ........................ 10-2011-0113837

(51) Int. Cl.
| | |
|---|---|
| *C09K 8/52* | (2006.01) |
| *C10L 3/10* | (2006.01) |
| *C08K 5/3415* | (2006.01) |
| *C08L 39/04* | (2006.01) |
| *C07D 207/04* | (2006.01) |
| *C07D 207/02* | (2006.01) |

(52) U.S. Cl.
CPC ................ *C08K 5/3415* (2013.01); *C09K 8/52* (2013.01); *C10L 3/107* (2013.01); *C07D 207/02* (2013.01); *C07D 207/04* (2013.01); *C08L 39/04* (2013.01); *C09K 2208/22* (2013.01)

(58) Field of Classification Search
USPC ......... 252/397, 399, 400.4, 400.41, 401, 403, 252/405, 407
See application file for complete search history.

(56) References Cited

U.S. PATENT DOCUMENTS

| | | | |
|---|---|---|---|
| 6,566,309 B1 * | 5/2003 | Klug et al. ...................... | 507/90 |
| 6,596,911 B2 * | 7/2003 | Przybylinski et al. .......... | 585/15 |

FOREIGN PATENT DOCUMENTS

WO          WO 9412761 A1 *  6/1994

OTHER PUBLICATIONS

Kim et al. Investigation of pyrrolidinium and morpholinium based ionic liquids into kinetic hydrate inhibitors on structure 1 methane hydrate. 7th International Conference on Gas Hyrdates, Jul. 2011.*
Kang et al. Investigation into the kinetic hydrate inhibitors of pyrrolidinium and morpholinium based ionic liquids on gas hydrate. ACS National Meeting. Mar. 2011.*
Kim et al. Pyrrolidinium cation based ionic liquids: New inhibitors for hydrate. Theories and Applications of Chem Eng. 2011. vol. 17. No. 2, Oct. 2011.*
Article—Kim et al., "Tuning Ionic Liquids for Hydrate Inhibition," *Chem. Commun.*, 2011, 47, pp. 6341-6343.

* cited by examiner

*Primary Examiner* — Tanisha Diggs
(74) *Attorney, Agent, or Firm* — Dority & Manning, P.A.

(57) ABSTRACT

Disclosed herein is a composition for inhibiting a gas hydrate formation, the composition including an ionic liquid compound and polyvinylcaprolactam. The composition can reduce the formation rate of a gas hydrate under the same environment in small quantity, thus remarkably extending the induction time of a gas hydrate formation.

1 Claim, 3 Drawing Sheets

COMPOSITION AND METHOD FOR INHIBITING GAS HYDRATE FORMATION

BACKGROUND OF THE INVENTION

1. Field of the Invention

The present invention is related to a gas hydrate inhibitor, a composition including the gas hydrate inhibitor and a method of inhibiting the formation of gas hydrate.

2. Description of the Related Art

Gas hydrates are ice-like solid compounds formed by entrapping "guest" molecules, such as methane, ethane, propane, carbon dioxide, nitrogen and the like, in a three-dimensional lattice structure built by hydrogen bonds of "host" water molecules. In general, the gas hydrates are formed and stably exist at low-temperature and high-pressure conditions.

Any solids in oil and gas industries are at least a nuisance for production, transport and processing of fluids. Thus, it is common for the gas hydrates to cause blockage problem of pipelines and other facilities, resulting in shutdown, loss of production, and risk of release of hydrocarbons into the environment. Consequently, the gas hydrates have attracted substantial interest on the suitable inhibition methods, in oil and gas industries in particular. Production of oil and natural gas and transport of the fluids are usually carried out in a deep ocean and thus the fluid passes through low temperature and high pressure conditions where the formation of the gas hydrate is favored. These produced fluids have some amount of accompanying water and dominantly contain gaseous and liquid hydrocarbons, which results in the formation of the solid gas hydrates. Aforementioned gas hydrate solids deposit on the surface of the pipelines, valves, and equipment so as to obstruct the secure transport and further processing of the fluids. In addition, the removal of the gas hydrates from the occurred parts requires a lot of time and cost that results in a loss of production during the remedy. For this reason, lots of efforts have been made to inhibit the formation of the gas hydrates in oil and natural gas industries.

Accordingly, the efficient and cost-effective inhibitors for the gas hydrate formation have been developed. However, the conventional inhibitors cannot sufficiently control and inhibit the formation of the gas hydrates. For example, too much amount of inhibitor is needed or insufficient retarding for the gas hydrate formation is happened. Thus, it is required a new gas hydrate which yield enhanced results over conventional gas hydrate inhibitors.

CITED REFERENCES

Patent Document

KR 2006-0112215

Non-Patent Document

Experimental Measurements of Hydrate Phase Equilibrium for Carbon Dioxide in the Presence of THF, Propylene Oxide, and 1,4-Dioxane (J. Chem. Eng. Data 2008, 53, 2833-2837)

SUMMARY OF THE INVENTION

Accordingly, the present invention intends to provide an inhibitor that can efficiently inhibit or retard the formation of a gas hydrate.

Further, the present invention intends to provide a composition for efficiently inhibiting or retarding the formation of a gas hydrate.

Further, the present invention intends to provide a method for efficiently inhibiting or retarding the formation of gas hydrates.

An aspect of the present invention provides a composition for inhibiting a gas hydrate formation, including: a compound represented by Chemical Formula 1 below; and polyvinylcaprolactam represented by Chemical Formula 2 below:

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $CH_3COO^-$, $NO_3^-$, or $BE_4^-$; and

[Chemical Formula 2]

wherein n is an integer of 5~100.

In some example embodiments of the present invention, $R_1$ may be a methyl group, an ethyl group or a propyl group, and $R_2$ may be a butyl group, a pentyl group, a hexyl group, a heptyl group, a hydroxymethyl group, a hydroxyethyl group or a hydroxypropyl group.

In some example embodiments of the present invention, $R_1$ may be a methyl group, and $R_2$ may be a propyl group, a butyl group, a pentyl group, a hydroxymethyl group, a hydroxyethyl group or a hydroxypropyl group.

In some example embodiments of the present invention, $Y^-$ may be $Cl^-$ or $BF_4^-$.

In some example embodiments of the present invention, the compound represented by Chemical Formula 1 may be at least one selected from the group consisting of N-hydroxyethyl-N-methylpyrrolidinium chloride, N-butyl-N-methylpyrrolidinium tetrafluoroborate, and N-hydroxyethyl-N-methylpyrrolidinium tetrafluoroborate.

Another aspect of the present invention provides a composition for inhibiting a gas hydrate formation, including: at least one selected from the group consisting of compounds represented by Chemical Formulae 3 to 5 below; and polyvinylcaprolactam represented by Chemical Formula 2 below:

[Chemical Formula 3]

[Chemical Formula 4]

[Chemical Formula 5]

wherein n is an integer of 5~100.

Still another aspect of the present invention provides a method of inhibiting a gas hydrate formation using a compound represented by Chemical Formula 1 below and polyvinylcaprolactam represented by Chemical Formula 2 below:

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $CH_3COO^-$, $NO_3^-$, or $BF_4^-$; and

[Chemical Formula 2]

wherein n is an integer of 5~100.

In some example embodiments of the present invention, the compound represented by Chemical Formula 1 may be any one of compounds represented by Formulae 3 to 5 below:

[Chemical Formula 3]

[Chemical Formula 4]

[Chemical Formula 5]

According to the present invention, the composition of the present invention can effectively inhibit a formation of a gas hydrate. That is, the composition of the present invention changes equilibrium conditions of the gas hydrate to allow the gas hydrate to be formed at a lower temperature and/or higher pressure and extends an induction time of a gas hydrate formation under the same temperature and pressure, thus inhibiting the formation of the gas hydrate in a small quantity.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention provides a gas hydrate inhibitor, comprising a compound represented by Chemical Formula 1 below:

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$.

In accordance with the present invention, the gas hydrate inhibitor means a compound that can prevent or delay the formation of the gas hydrate.

In accordance with the present invention, the compound represented by Chemical Formula 1 can prevent or delay the formation of the gas hydrate regardless of the kind of gas. That is, the compound represented by Chemical Formula 1 can prevent or delay the formation of the gas hydrate regardless of the kind of gas entrapped inside a cavity formed by hydrogen bonded water molecules. Examples of the gas may include hydrocarbons having a low-molecular-weight. For example, the gas may include methane, ethane, propane, butane, pentane, or a mixture thereof, preferably, methane.

The compound represented by Chemical Formula 1 may be an ionic liquid compound. The ionic liquid compound may be a salt in a liquid state and have a melting point below about 100° C. The ionic liquid compound may include a cation and an anion. The physical and chemical characteristics thereof can be adjusted by changing the property and kind of the cation and anion.

The compound represented by Chemical Formula 1 includes pyrrolidinium as the cation, and includes $OH^-$, $Cl^-$, $Br^-$, $I^-$, $CH_3COO^-$, $NO_3^-$ or $BF_4^-$ as an anion.

The compound represented by Chemical Formula 1 may function as both a thermodynamic inhibitor and a kinetic inhibitor in the formation of the gas hydrate.

In the formation of the gas hydrate, the thermodynamic inhibitor may change an equilibrium dissociation condition of the gas hydrate. That is, the thermodynamic inhibitor, which shifts an equilibrium dissociation curve of the gas hydrate to a lower temperature and/or a higher pressure, may generally enable the gas hydrate to be formed at a lower temperature and/or a higher pressure.

Further, in the formation of the gas hydrate, the kinetic inhibitor may retard a gas hydrate nucleation and/or growth at the same temperature and at the same pressure without changing the equilibrium condition of the gas hydrate. That is, the kinetic inhibitor may extend an induction time of the gas hydrate formation at the same temperature and at the same pressure.

The compound represented by Chemical Formula 1 may serve as both the thermodynamic inhibitor and the kinetic inhibitor in the formation of the gas hydrate. The compound represented by Chemical Formula 1 may change the equilibrium condition of the gas hydrate so that the gas hydrate may be formed at a lower temperature and/or a higher pressure. Further, the compound represented by Chemical Formula 1 may retard the formation of the gas hydrate at the same temperature and at the same pressure by slowing down the gas hydrate nucleation and/or growth and thus the induction time of the gas hydrate formation may be extended. Therefore, when the compound represented by Chemical Formula 1 is used in oil and natural gas industries, the gas hydrate may be formed at a lower temperature and/or a higher pressure and also the formation of the gas hydrate may be delayed at the same temperature and at the same pressure to effectively inhibit the formation of the gas hydrate in a small quantity for production, processing and transportation of oil and natural gas.

In accordance with the present invention, the compound represented by Chemical Formula 1 may decrease the equilibrium temperature of the gas hydrate by about 1.3~1.7K at the same pressure, and may extend the induction time of the gas hydrate formation at the same temperature and at the same pressure.

In the compound represented by Chemical Formula 1 of the present invention, $R_1$ may be a methyl group, an ethyl group or a propyl group, and $R_2$ may be a butyl group, a pentyl group, a hexyl group, a heptyl group, a hydroxymethyl group, a hydroxyethyl group or a hydroxypropyl group. Preferably, $R_1$ may be a methyl group, and $R_2$ may be a propyl group, a butyl group, a pentyl group, a hydroxymethyl group, a hydroxyethyl group or a hydroxypropyl group.

Further, in the compound represented by Chemical Formula 1 of the present invention, $Y^-$ may be $Cl^-$ or $BF_4^-$.

In accordance with the present invention, the compound represented by Chemical Formula 1 may be selected from compounds represented by Chemical formulae 2 to 4.

[Chemical Formula 2]

The compound represented by Chemical Formula 2 may be N-hydroxyethyl-N-methylpyrrolidinium chloride.

[Chemical Formula 3]

The compound represented by Chemical Formula 3 may be N-butyl-N-methylpyrrolidinium tetrafluoroborate.

[Chemical Formula 4]

The compound represented by Chemical Formula 4 may be N-hydroxyethyl-N-methylpyrrolidinium tetrafluoroborate.

The compound represented by Chemical Formula 1 may be introduced into a place where the formation of the gas hydrate is to be inhibited in an amount of about 0.01~about 30 w %. When the amount of the compound is more than 30 wt %, it is too expensive to practically apply it, and particularly, when it is applied to a pipe or the like, it causes the pipe or the like to corrode, foam or precipitate. Therefore, the compound may be introduced into the place where the formation of the gas hydrate is to be inhibited in an amount of about 0.01~ about 30 w %, and preferably 0.05~11 wt %.

The present invention provides a composition for inhibiting a gas hydrate formation, including: a compound represented by Chemical Formula 1 below; and polyvinylcaprolactam represented by Chemical Formula 2 below:

[Chemical Formula 1]

[[Chemical Formula 5]]

In Chemical Formula 1, $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$. Preferably, $R_1$ may be a methyl group, an ethyl group or a propyl group, and $R_2$ may be a butyl group, a pentyl group, a hexyl group, a heptyl group, a hydroxymethyl group, a hydroxyethyl group, or a hydroxypropyl group. More preferably, $R_1$ may be a methyl group, and $R_2$ may be a propyl group, a butyl group, a pentyl group, a hydroxymethyl group, a hydroxyethyl group, or a hydroxypropyl group. Further, $Y^-$ may be $Cl^-$ or $BF_4^-$.

In Chemical Formula 5, n is an integer of 5~100, and preferably 10~60. The weight average molecular weight of polyvinylcaprolactam represented by Chemical Formula 5 may be 2000~8000, preferably 4000~6000, and more preferably 5000.

In accordance with the composition of the present invention, when the compound represented by Chemical Formula 1 is used together with the polyvinylcaprolactam represented by Chemical Formula 5, the formation time of a gas hydrate, particularly, methane hydrate can be remarkably retarded in the same amount, compared to when the compound represented by Chemical Formula 1 and the polyvinylcaprolactam represented by Chemical Formula 5 are each independently used.

The composition including the compound represented by Chemical Formula 1 and the polyvinylcaprolactam represented by Chemical Formula 5 may be introduced into a place where the formation of the gas hydrate is to be inhibited in an amount of 0.01~30 wt %. When the amount of the composition is more than 30 wt %, it is too expensive to practically apply it, and particularly, when it is applied to a pipe or the like, it causes the pipe or the like to corrode, foam or precipitate. Therefore, the composition may be introduced into a place where the formation of the gas hydrate is to be inhibited in an amount of 0.01~30 wt %.

In accordance with the present invention, the compound represented by Chemical Formula 1 may be at least one selected from compounds represented by Chemical formulae 2 to 4 below.

[Chemical Formula 2]

The compound represented by Chemical Formula 2 may be N-hydroxyethyl-N-methylpyrrolidinium chloride.

[Chemical Formula 3]

The compound represented by Chemical Formula 3 may be N-butyl-N-methylpyrrolidinium tetrafluoroborate.

[Chemical Formula 4]

The compound represented by Chemical Formula 4 may be N-hydroxyethyl-N-methylpyrrolidinium tetrafluoroborate.

The composition including polyvinylcaprolactam represented by Chemical Formula 5 and at least one selected from N-hydroxyethyl-N-methylpyrrolidinium chloride represented by Chemical Formula 2, N-butyl-N-methylpyrrolidinium tetrafluoroborate represented by Chemical Formula 3 and N-hydroxyethyl-N-methylpyrrolidinium tetrafluoroborate represented by Chemical Formula 4 can remarkably delay the formation of methane hydrate. That is, when the composition including at least one selected from compounds represented by Chemical formulae 2 to 4 and polyvinylcaprolactam represented by Chemical Formula 5 is used, the formation time of methane hydrate can be remarkably delayed two times or more in the same amount, compared to when at least one selected from compounds represented by Chemical formulae 2 to 4 and polyvinylcaprolactam represented by Chemical Formula 5 are each independently used.

The present invention provides a method of inhibiting a gas hydrate formation using a compound represented by Chemical Formula 1 below:

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$.

In accordance with the present invention, the compound represented by Chemical Formula 1 may be introduced into a place where the formation of the gas hydrate is undesirable to change an equilibrium condition of the gas hydrate into a lower temperature and/or a higher pressure. Thus, the compound represented by Chemical Formula 1 may effectively inhibit the formation of the gas hydrate in a place which has a lower temperature and/or a higher pressure than those of the equilibrium condition of the gas hydrate. Further, the compound may be introduced into a place where the formation of the gas hydrate is undesirable to retard the formation of the gas hydrate at a same temperature and a same pressure. Thus, the compound may effectively extended an induction time of the gas hydrate formation in a place which has a temperature and a pressure at which the formation of the gas hydrate may be favored.

In accordance with the present invention, the compound represented by Chemical Formula 1 may be at least one selected from compounds represented by Chemical formulae 2 to 4 below.

[Chemical Formula 2]

The compound represented by Chemical Formula 2 may be N-hydroxyethyl-N-methylpyrrolidinium chloride.

[Chemical Formula 3]

The compound represented by Chemical Formula 3 may be N-butyl-N-methylpyrrolidinium tetrafluoroborate.

[Chemical Formula 4]

The compound represented by Chemical Formula 4 may be N-hydroxyethyl-N-methylpyrrolidinium tetrafluoroborate.

In accordance with the method of the present invention, one or more of compounds represented by Chemical Formula 1 may be used. For example, the formation of a gas hydrate can be inhibited using both N-butyl-N-methylpyrrolidinium tetrafluoroborate represented by Chemical Formula 3 and N-hydroxyethyl-N-methylpyrrolidinium tetrafluoroborate represented by Chemical Formula 4.

In accordance with the method of the present invention, another compound may be additionally used as a gas hydrate inhibitor together with the compound represented by Chemical Formula 1. For example, a methanol, ethanol, n-propanol, isopropanol, ethylene glycol, propylene glycol, potassium formate, methylacrylamide, acrylamide, N-butylacrylamide, sodium chloride, polyvinylidene, or a mixture thereof may be used together with the compound represented by Chemical Formula 1 as a gas hydrate inhibitor.

The present invention provides a method of inhibiting a gas hydrate formation using a compound represented by Chemical Formula 1 below and polyvinylcaprolactam represented by Chemical Formula 5 below:

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$; and

[Chemical Formula 5]

wherein n is an integer of 5~100, and preferably 10~60.

The weight average molecular weight of polyvinylcaprolactam represented by Chemical Formula 5 may be 2000~8000, preferably 4000~6000, and more preferably 5000.

In accordance with the present invention, the composition including the compound represented by Chemical Formula 1 and the polyvinylcaprolactam represented by Chemical Formula 5 can remarkably delay the formation of a gas hydrate.

The compound including the compound represented by Chemical Formula 1 and the polyvinylcaprolactam represented by Chemical Formula 5 may be introduced into a place where the formation of the gas hydrate is to be inhibited in an amount of 0.01~30 wt %. When the amount of the composition is more than 30 wt %, it is too expensive to practically apply it, and particularly, when it is applied to a pipe or the like, it causes the pipe or the like to corrode, foam or precipitate. Therefore, the composition may be introduced into a place where the formation of the gas hydrate is to be inhibited in an amount of 0.01~30 wt %, and preferably 0.05~11 wt %.

In accordance with the method of the present invention, the compound represented by Chemical Formula 1 may be selected from compounds represented by Chemical formulae 2 to 4 below.

[Chemical Formula 2]

The compound represented by Chemical Formula 2 may be N-hydroxyethyl-N-methylpyrrolidinium chloride.

[Chemical Formula 3]

The compound represented by Chemical Formula 3 may be N-butyl-N-methylpyrrolidinium tetrafluoroborate.

[Chemical Formula 4]

The compound represented by Chemical Formula 4 may be N-hydroxyethyl-N-methylpyrrolidinium tetrafluoroborate.

In accordance with the method of the present invention, the composition may include at least one of the compounds represented by Chemical formulae 2 to 4.

In accordance with the method of the present invention, the composition including the polyvinylcaprolactam represented by Chemical formula 5 and at least one of the compounds represented by Chemical formulae 2 to 4 can remarkably delay the formation of a gas hydrate, particularly, methane hydrate.

In accordance with the method of the present invention, another gas hydrate inhibitor may be additionally used together with the composition including the compound represented by Chemical formula 1 and the polyvinylcaprolactam represented by Chemical formula 5 to inhibit the formation of a gas hydrate. For example, methanol, ethanol, n-propanol, isopropanol, ethylene glycol, propylene glycol, potassium formate, methylacrylamide, acrylamide, N-butylacrylamide, sodium chloride, polyvinylidene, or a mixture thereof may be used together with the composition of the present invention.

Hereinafter, the present invention will be described in more detail with reference to the following Examples. However, these Examples are set forth to more easily understand the present invention, and the scope of the present invention is not limited thereto.

The following reagent and solvent is commercially available from Sigma-Aldrich Korea Corp., and the following $^1$H-NMR data are values measured using Advance 400FT-NMR (400 MHz) manufactured by Bruker Co., Ltd.

PREPARATION EXAMPLE 1

Preparation of N-hydroxyethyl-N-methylpyrrolidinium chloride

About 200 mL of acetonitrile (manufactured by Junsei Co., Ltd. in Japan) was mixed with about 52.7 mL (0.5 mol) of methylpyrrolidone (manufactured by Fluka Co., Ltd.) under a nitrogen atmosphere to form a liquid mixture. Subsequently, about 36.5 mL (0.55 mol) of 2-chloroethanol (manufactured by Aldrich Co., Ltd.) was added to the liquid mixture drop by drop to form a mixed solution. Subsequently, the mixed solution was stirred at about 65° C. for about 48 hours under a nitrogen atmosphere, and was then stored at about 4° C. for about 12 hours to form crystals. After a supernatant was removed from the mixed solution, the crystals were dried at a temperature of about 35° C. and a pressure of about 0.2 atm for about 12 hours using a vacuum evaporator to remove a solvent therefrom. Subsequently, in order to remove impurity, the dried crystals were dissolved in about 100 mL of acetone, and were then stirred at a temperature of about 25° C. and a pressure of about 1 atm for about 30 minutes to form a solution. The solution was stored at about 4° C. for about 12 hours to form crystals again. After a supernatant was removed from the solution, the crystals were dried at a temperature of about 35° C. and a pressure of about 0.2 atm for about 12 hours using a vacuum evaporator. These processes were repeatedly conducted three times to obtain N-hydroxyethyl-N-methylpyrrolidinium chloride at a yield of about 60%.

$^1$H-NMR (400 MHz, D$_2$O): δ 4.698 (s, 2H), 3.891~3.854 (m, 2H), 3.438~3.335 (m, 7H), 2.929 (s, OH), 2.042 (s, 4H)

PREPARATION EXAMPLE 2

Preparation of N-hydroxyethyl-N-methylpyrrolidinium tetrafluoroborate

About 200 mL of acetonitrile (manufactured by Junsei Co., Ltd. in Japan) was mixed with about 52.7 mL (0.5 mol) of methylpyrrolidone (manufactured by Fluka Co., Ltd.) under a nitrogen atmosphere to form a liquid mixture. Subsequently, about 36.5 mL (0.55 mol) of 2-chloroethanol (manufactured by Aldrich Co., Ltd.) was added to the liquid mixture drop by drop to form a mixed solution. Subsequently, the mixed solution was stirred at about 65° C. for about 48 hours under a nitrogen atmosphere, and was then stored at about 4° C. for about 12 hours to form crystals. After a supernatant was removed from the mixed solution, the crystals were dried at a temperature of about 35° C. and a pressure of about 0.2 atm for about 12 hours using a vacuum evaporator to remove a solvent therefrom. Subsequently, in order to remove impurities, the dried crystals were dissolved in about 100 mL of acetone, and then were stirred at a temperature of about 25° C. and a pressure of about 1 atm for about 30 minutes to form a solution. The solution was stored at about 4° C. for about 12 hours to form crystals again. After a supernatant was removed from the solution, the crystals were dried at a temperature of about 35° C. and a pressure of about 0.2 atm for about 12 hours using a vacuum evaporator. These processes were repeatedly conducted three times to obtain N-hydroxyethyl-N-methylpyrrolidinium chloride at a yield of about 75%.

Subsequently, about 36.9 g (0.3 mol) of the obtained N-hydroxyethyl-N-methylpyrrolidinium chloride and about 32.3 g (0.3 mol) of sodium tetrafluoroborate were dissolved in about 200 mL of acetone, and were then stirred at a temperature of about 25° C. and a pressure of about 1 atm for about 48 hours under a nitrogen atmosphere to form a mixed solution containing sodium chloride. The mixed solution was filtered by a filter paper to remove sodium chloride therefrom to obtain a liquid. Then, the obtained liquid, about 50 mL of dichloromethane, and about 0.5 mL of distilled water were shaken in a separating funnel for about 10 minutes and thus uniformly mixed with each other to form a mixed solution, and then the mixed solution was left at a temperature of 25° C. and a pressure of about 1 atm for about 48 hours. When the mixed solution was layer-separated in the separating funnel according to a density, the liquid located in a lower portion of the separating funnel was removed, and the liquid located in an upper portion thereof was obtained. These processes were repeatedly conducted three times to obtain a final liquid. The final liquid was left in a vacuum oven at about 35° C. for about 48 hours to further remove water therefrom, thereby obtaining N-hydroxyethyl-N-methylpyrrolidinium tetrafluoroborate at a yield of about 65%.

$^1$H-NMR (400 MHz, DMSO): δ 5.3~5.28 (t, 2H), 3.83~3.82 (q, 2H), 3.51~3.39 (m, 7H), 2.08~2.07 (m, 4H)

PREPARATION EXAMPLE 3

Preparation of N-butyl-N-methylpyrrolidinium tetrafluoroborate

About 200 mL of acetonitrile (manufactured by Junsei Co., Ltd. in Japan) was mixed with about 52.7 mL (0.5 mol) of methylpyrrolidone (manufactured by Fluka Co., Ltd.) under a nitrogen atmosphere to form a liquid mixture. Subsequently, about 58.6 mL (0.55 mol) of 2-bromobutane (manufactured by Aldrich Co., Ltd.) was added into the liquid mixture drop by drop to form a mixed solution. Subsequently, the mixed solution was stirred at about 65° C. for about 48 hours under a nitrogen atmosphere, and was then stored at about 4° C. for about 12 hours to form crystals. After a supernatant was removed from the mixed solution, the crystals were dried at a temperature of about 35° C. and a pressure of about 0.2 atm for about 12 hours using a vacuum evaporator to remove a solvent therefrom. Subsequently, in order to remove impurities, the dried crystals were dissolved in about 100 mL of acetone, and were then stirred at a temperature of about 25° C. and a pressure of about 1 atm for about 30 minutes to form a solution. The solution was left at 4° C. for about 12 hours to form crystals again. After a supernatant was removed from the solution, the crystals were dried at a temperature of about 35° C. and a pressure of about 0.2 atm for about 12 hours using a vacuum evaporator. These processes were repeatedly conducted three times to obtain N-butyl-N-methylpyrrolidinium bromide at a yield of about 60%.

Subsequently, about 24.8 g (0.3 mol) of the obtained N-butyl-N-methylpyrrolidinium bromide and about 32.3 g (0.3 mol) of sodium tetrafluoroborate were dissolved in about 200 mL of acetone, and were then stirred at a temperature of about 25° C. and a pressure of about 1 atm for about 48 hours under a nitrogen atmosphere to form a mixed solution containing sodium bromide. The mixed solution was filtered by a filter paper to remove sodium bromide therefrom to obtain a liquid. Then, the obtained liquid, about 50 mL of dichloromethane, and about 0.5 mL of distilled water were shaken in a separating funnel for about 10 minutes and thus uniformly mixed with each other to form a mixed solution, and then the mixed solution was left at a temperature of about 25° C. and a pressure of about 1 atm for about 48 hours. When the mixed solution was layer-separated in the separating funnel according to a density, the liquid located in a lower portion of the separating funnel was removed, and the liquid located in an upper portion thereof was obtained. These processes were repeatedly conducted three times to obtain a final liquid. The final liquid was left in a vacuum oven at about 35° C. for about 48 hours to further remove water therefrom, thereby obtaining N-butyl-N-methylpyrrolidinium tetrafluoroborate at a yield of about 45%.

$^1$H-NMR (400 MHz, $D_2O$): δ 3.39 (s, 4H), 3.24~3.20 (m, 2H), 2.93 (s, 3H), 2.10 (s, 4H), 1.71~1.63 (m, 2H), 1.31~1.25 (m, 2H), 0.86~0.82 (t, 3H)

PREPARATION EXAMPLE 4

Preparation of polyvinylcaprolactam

Polyvinylcaprolactam was obtained by volatilizing ethanol from Luviskol Plus (manufactured by BASF Corp.).

500 g of Luviskol Plus (manufactured by BASF Corp.) was put into a round-bottom flask, a pressure of 100 torr was applied to the flask using a vacuum evaporator, and then the flask was immersed in an oil bath to volatilize ethanol. Subsequently, the residue product was left for 24 hours in a vacuum oven at a temperature of 50° C. and a pressure of 65 torr to additionally remove the ethanol, thereby obtaining polyvinylcaprolactam having a weight average molecular weight of 5000.

EXAMPLES (1) Example 1

The N-hydroxyethyl-N-methylpyrrolidinium chloride of Preparation Example 1 was dissolved in distilled water to obtain a composition 1 including 1 wt % of N-hydroxyethyl-N-chloride.

(2) Example 2

The N-hydroxyethyl-N-methylpyrrolidinium tetrafluoroborate of Preparation Example 2 was dissolved in distilled water to obtain a composition 2 including 1 wt % of N-hydroxyethyl-N-methylpyrrolidinium tetrafluoroborate.

(3) Example 3

The N-butyl-N-methylpyrrolidinium tetrafluoroborate of Preparation Example 3 was dissolved in distilled water to obtain a composition 3 including 1 wt % of N-butyl-N-methylpyrrolidinium tetrafluoroborate.

(4) Example 4

The N-hydroxyethyl-N-methylpyrrolidinium chloride of Preparation Example 1 was dissolved in distilled water to obtain a composition 4 including 10 wt % of N-hydroxyethyl-N-methylpyrrolidinium chloride.

(5) Example 5

The N-hydroxyethyl-N-methylpyrrolidinium tetrafluoroborate of Preparation Example 2 was dissolved in distilled water to obtain a composition 5 including 10 wt % of N-hydroxyethyl-N-methylpyrrolidinium tetrafluoroborate.

(6) Example 6

The N-butyl-N-methylpyrrolidinium tetrafluoroborate of Preparation Example 3 was dissolved in distilled water to obtain a composition 6 including 10 wt % of N-butyl-N-methylpyrrolidinium tetrafluoroborate.

(7) Example 7

The N-hydroxyethyl-N-methylpyrrolidinium chloride of Preparation Example 1 and the polyvinylcaprolactam of Preparation Example 4 were dissolved in distilled water to obtain a composition 7 including 0.5 wt % of N-hydroxyethyl-N-methylpyrrolidinium chloride and 0.5 wt % of polyvinylcaprolactam.

(8) Example 8

The N-hydroxyethyl-N-methylpyrrolidinium tetrafluoroborate of Preparation Example 2 and the polyvinylcaprolactam of Preparation Example 4 were dissolved in distilled water to obtain a composition 8 including 0.5 wt % of N-hydroxyethyl-N-methylpyrrolidinium tetrafluoroborate and 0.5 wt % of polyvinylcaprolactam.

(9) Example 9

The N-butyl-N-methylpyrrolidinium tetrafluoroborate of Preparation Example 3 and the polyvinylcaprolactam of Preparation Example 4 were dissolved in distilled water to obtain a composition 9 including 0.5 wt % of N-butyl-N-methylpyrrolidinium tetrafluoroborate and 0.5 wt % of polyvinylcaprolactam.

(10) Example 10

The N-hydroxyethyl-N-methylpyrrolidinium chloride of Preparation Example 1 was dissolved in distilled water to obtain a composition 10 including 3 wt % of N-hydroxyethyl-N-methylpyrrolidinium chloride.

(11) Example 11

The N-hydroxyethyl-N-methylpyrrolidinium tetrafluoroborate of Preparation Example 2 was dissolved in distilled water to obtain a composition 11 including 3 wt % of N-hydroxyethyl-N-methylpyrrolidinium tetrafluoroborate.

(12) Example 12

The N-butyl-N-methylpyrrolidinium tetrafluoroborate of Preparation Example 3 was dissolved in distilled water to obtain a composition 12 including 3 wt % of N-butyl-N-methylpyrrolidinium tetrafluoroborate.

(13) Example 13

The N-hydroxyethyl-N-methylpyrrolidinium chloride of Preparation Example 1 and the polyvinylcaprolactam of Preparation Example 4 were dissolved in distilled water to obtain a composition 13 including 3 wt % of N-hydroxyethyl-N-methylpyrrolidinium chloride and 0.5 wt % of polyvinylcaprolactam.

(14) Example 14

The N-hydroxyethyl-N-methylpyrrolidinium tetrafluoroborate of Preparation Example 2 and the polyvinylcaprolactam of Preparation Example 4 were dissolved in distilled water to obtain a composition 14 including 3 wt % of N-hydroxyethyl-N-methylpyrrolidinium tetrafluoroborate and 0.5 wt % of polyvinylcaprolactam.

(15) Example 15

The N-butyl-N-methylpyrrolidinium tetrafluoroborate of Preparation Example 3 and the polyvinylcaprolactam of Preparation Example 4 were dissolved in distilled water to obtain a composition 15 including 3 wt % of N-butyl-N-methylpyrrolidinium tetrafluoroborate and 0.5 wt % of polyvinylcaprolactam.

COMPARATIVE EXAMPLEs (1) Comparative Example 1

The 1-ethyl-3-methylimidazolinium tetrafluoroborate (manufactured by C-RTI Corp.) was dissolved in distilled water to obtain a comparative composition 1 including 10 wt % of 1-ethyl-3-methylimidazolinium tetrafluoroborate.

(2) Comparative Example 2

The polyvinylcaprolactam of Preparation Example 4 was dissolved in distilled water to obtain a comparative composition 2 including 1 wt % of polyvinylcaprolactam.

The components included in the compositions of Examples and Comparative Examples and amounts thereof are given in Table 1 below.

TABLE 1

Components included in the compositions of Examples 1 to 9 and Comparative Examples 1 and 2 and amounts thereof

| | Component | Amount (wt %) |
|---|---|---|
| Example 1 | N-hydroxyethyl-N-methylpyrrolidinium chloride | 1 |
| Example 2 | N-hydroxyethyl-N-methylpyrrolidinium tetrafluoroborate | 1 |
| Example 3 | N-butyl-N-methylpyrrolidinium tetrafluoroborate | 1 |
| Example 4 | N-hydroxyethyl-N-methylpyrrolidinium chloride | 10 |
| Example 5 | N-hydroxyethyl-N-methylpyrrolidinium tetrafluoroborate | 10 |
| Example 6 | N-butyl-N-methylpyrrolidinium tetrafluoroborate | 10 |
| Example 7 | N-hydroxyethyl-N-methylpyrrolidinium chloride polyvinylcaprolactam | 0.5 0.5 |
| Example 8 | N-hydroxyethyl-N-methylpyrrolidinium tetrafluoroborate polyvinylcaprolactam | 0.5 0.5 |
| Example 9 | N-butyl-N-methylpyrrolidinium tetrafluoroborate polyvinylcaprolactam | 0.5 0.5 |
| Example 10 | N-hydroxyethyl-N-methylpyrrolidinium chloride | 3 |
| Example 11 | N-hydroxyethyl-N-methylpyrrolidinium tetrafluoroborate | 3 |
| Example 12 | N-butyl-N-methylpyrrolidinium tetrafluoroborate | 3 |
| Example 13 | N-hydroxyethyl-N-methylpyrrolidinium chloride polyvinylcaprolactam | 3 0.5 |
| Example 14 | N-hydroxyethyl-N-methylpyrrolidinium tetrafluoroborate polyvinylcaprolactam | 3 0.5 |
| Example 15 | N-butyl-N-methylpyrrolidinium tetrafluoroborate polyvinylcaprolactam | 3 0.5 |
| Comparative Example 1 | 1-ethyl-3-methylimidazolinium tetrafluoroborate | 10 |
| Comparative Example 2 | polyvinylcaprolactam | 1 |

EXPERIMENTAL EXAMPLE 1

Ascertainment of Change in Phase Equilibrium Temperature and Pressure of Methane Hydrate Using The Compositions of Examples 4 to 6

1. Providing an Experimental System

A high-pressure reactor having an inner volume of about 350 cc and made of stainless steel was provided. The high-pressure reactor was disposed in a water tank provided at the outside thereof with a cooler for a temperature control. A sapphire observation window was provided over the high-temperature reactor in order to observe whether a hydrate was formed and a pressure transducer and a thermocouple was provided in the high-temperature reactor in order to measure the temperature and pressure in the high-pressure reactor. This experimental system including the high-pressure reactor and the water tank and measuring the phase equilibrium temperature and pressure of the hydrate in the formation and dissociation thereof is disclosed in the paper "Hydrate phase equilibria of the guest mixtures containing $CO_2$, $N_2$ and tetrahydrofuran (Fluid Phase Equilibria 185 (2001), 101-109)".

2. Measuring the Phase Equilibrium Temperature and Pressure of a Methane Hydrate in the Dissociation Thereof.

An aqueous solution including 90 g of the composition 4 of Example 4 containing 10 wt % of N-hydroxyethyl-N-methylpyrrolidinium chloride was put into a high-pressure reactor, and then the high-pressure reactor was tightly closed. Air remaining in the high-pressure reactor was removed, and then a methane gas was injected into the high-pressure reactor until the pressure in the high-pressure reactor was about 70 atm. Subsequently, the high-pressure reactor was put into the temperature-controllable water tank, and then the pressure and temperature in the high-pressure reactor were measured in real time using a pressure gauge and a thermometer connected to the high-pressure reactor.

The aqueous solution in the high-pressure reactor was stirred, and simultaneously the water tank was cooled to reduce the temperature of the high-pressure reactor. When the pressure in the high-pressure reactor rapidly dropped and the temperature thereof increased, that means the formation of gas hydrate had occurred. After that, the system remained as it was to allow the growth of gas hydrate crystals. Thereafter, whether or not the aqueous solution in the high-pressure reactor was completely converted into the methane hydrate was observed through the sapphire observation window.

After the aqueous solution in the high-pressure reactor was completely converted into the methane hydrate, the water tank was heated at a rate of about 0.2° C./hr. According to the temperature increase, methane captured in the gas hydrate was retrieved therefrom, and simultaneously the pressure in the high-pressure reactor was continuously increased. The increase of the pressure in the high-pressure reactor becomes slow when methane hydrate is completely dissociated. Thus the pressure and temperature in the high-pressure reactor were measured at the time that the increase rate of the pressure in the high-pressure reactor started to decrease so that the phase equilibrium temperature and pressure of the methane hydrate were measured.

Further, the phase equilibrium temperature and pressure of the methane hydrate were measured in the same manner as above using the composition 5 of Example 5 including N-hydroxyethyl-N-methylpyrrolidinium tetrafluoroborate and the composition 6 of Example 6 including N-butyl-N-methylpyrrolidinium tetrafluoroborate instead of the composition 4 of Example 4 including N-hydroxyethyl-N-methylpyrrolidinium chloride. Further, the phase equilibrium temperature and pressure of methane hydrate were measured in the same manner as above using pure water. The phase equilibrium temperatures and pressures of the methane hydrate, measured using the compositions of Examples 4 to 6 and water, are illustrated in FIG. 1.

Figure 1:
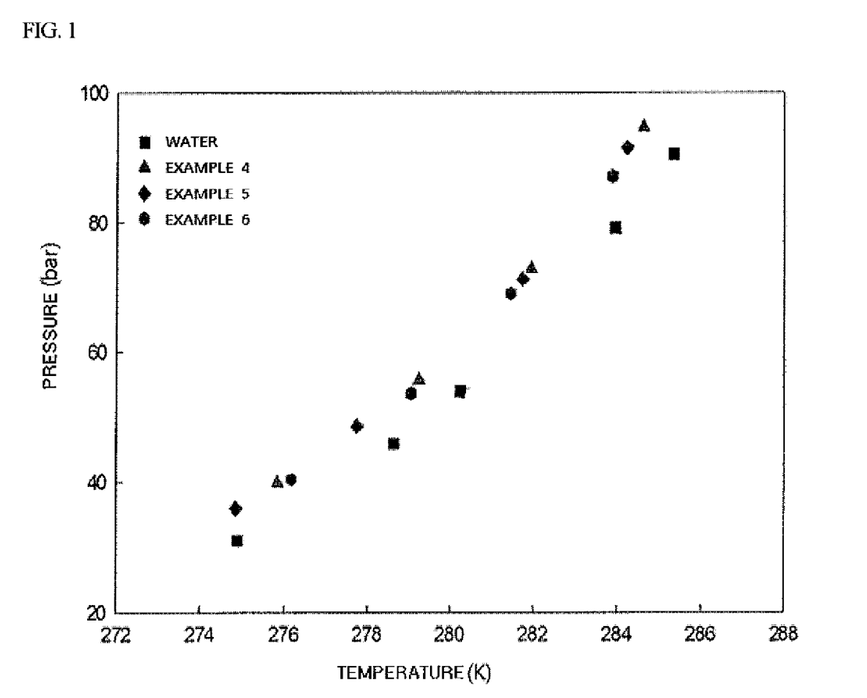
FIG. 1 is a graph showing a change in equilibrium dissociation conditions of a methane hydrate according to the ionic liquid compound of the present invention.

As illustrated in FIG. 1, comparing the aqueous solutions respectively including the compositions of Examples 4 to 6 with the aqueous solution not including any one of the compounds of Preparation Examples 1 to 3, methane hydrate was formed at a higher pressure under the same temperature, and was formed at a lower temperature under the same pressure. Therefore, when the compounds of Preparation Examples 1 to 3 were applied into oil and natural gas industries, the formation of the methane hydrate was inhibited until the pressure and temperature reached a lower temperature and/or higher pressure, compared to those of the equilibrium conditions in case that the compounds of Preparation Examples 1 to 3 were not applied.

EXPERIMENTAL EXAMPLE 2

Measuring a Delay of a Formation of a Methane Hydrate Using the Compositions of Examples 4 to 6

1. Providing an Experimental System

An experimental system including a high-pressure reactor and a water tank was provided as used in Experimental Example 1.

2. Measuring an Induction Time of a Methane Hydrate Formation

About 90 g of an aqueous solution including the composition 4 of Example 4 containing 10 wt % of N-hydroxyethyl-N-methylpyrrolidinium chloride was put into a high-pressure reactor, and then the high-pressure reactor was tightly closed. Air remaining in the high-pressure reactor was removed, and then a methane gas was injected into the high-pressure reactor until the pressure in the high-pressure reactor was 70 atm.

Subsequently, the high-pressure reactor was put into a temperature-controllable water tank, and then the pressure and temperature in the high-pressure reactor were measured in real time using a pressure gauge and a thermometer connected to the high-pressure reactor.

After the temperature in the high-pressure reactor was set to about 0.5° C., the aqueous solution was started to stir the content continuously at a rotation speed of about 600 rpm to uniformly disperse N-hydroxyethyl-N-methylpyrrolidinium chloride in the aqueous solution while the temperature of the aqueous solution was maintained constant.

When methane hydrate is formed, the temperature in the high-pressure reactor is rapidly increased, and the pressure in the high-pressure reaction is rapidly decreased. Therefore, the change of the pressure and temperature in the high-pressure reactor was continuously measured. When a rapid temperature increase and a pressure drop thereof were observed, a time from the beginning of stirring until then was measured and the time from stirrer start until then was defined as an induction time of a methane hydrate formation.

The induction time of the methane hydrate formation was measured in the same manner as above using the composition 5 of Example 5 including N-hydroxyethyl-N-methylpyrrolidinium tetrafluoroborate and the composition 6 of Example 6 including N-butyl-N-methylpyrrolidinium tetrafluoroborate instead of using the composition 4 of Example 4 including N-hydroxyethyl-N-methylpyrrolidinium chloride. Further, the induction time of the methane hydrate formation was measured in the same manner as above using the comparative composition 1 of Comparative Example 1 including 1-ethyl-3-methylimidazolinium tetrafluoroborate instead of using the composition 4 of Example 4 including N-hydroxyethyl-N-methylpyrrolidinium chloride. The induction times of the methane hydrate formation, measured using the compositions of Examples 4 to 6 and Comparative Example 1, are illustrated in FIG. 2.

Figure 2:
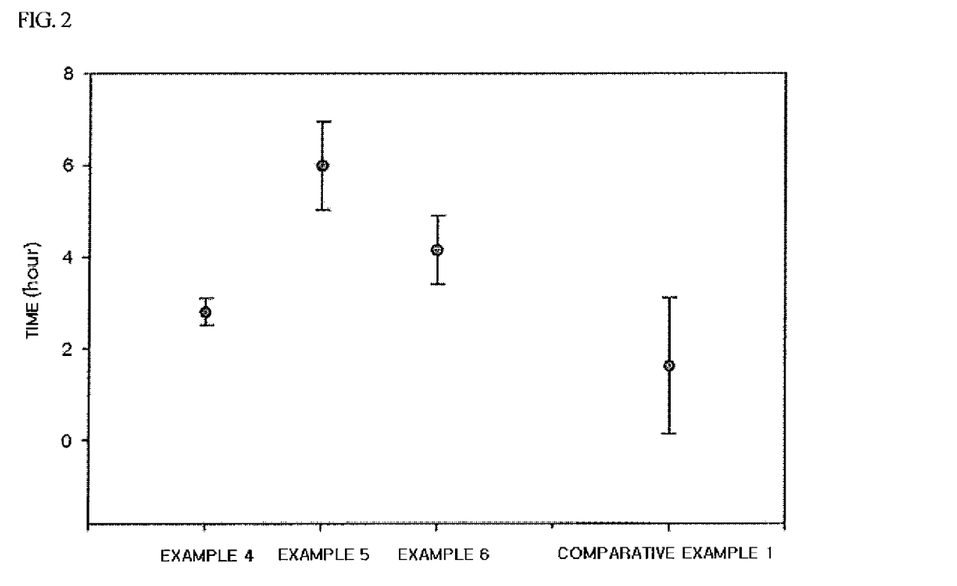
FIG. 2 is a graph showing a delay of a methane hydrate formation according to the ionic liquid compound of the present invention.

As illustrated in FIG. 2, when the compositions of Examples 4 to 6 were used, it can be seen that the induction times of the methane hydrate formation were extended by two hours or more. In particular, when the composition of Example was used, it can be seen that the induction time of the methane hydrate formation was extended by about six hours, thus effectively retarding the formation of the methane hydrate. In contrast, when the comparative composition of the Comparative Example 1 was used, it can be seen that the induction time of the methane hydrate formation was extended extended by less than two hours. Therefore, when the compounds of Preparation Examples 1 to 3 were applied to the place having a predetermined temperature and pressure at which the formation of the methane hydrate is favored, it can be seen that the formation of the methane hydrate can be effectively delayed.

EXPERIMENTAL EXAMPLE 3

Measuring a Delay of a Formation Of a Methane Hydrate Using the Compositions of Examples 1 to 3, Examples 7 to 15 and Comparative Example 2

1. Providing an Experimental System

An experimental system including a high-pressure reactor and a water tank was provided as used in Experimental Example 1.

2. Measuring an Induction Time of a Methane Hydrate Formation

The induction times of the methane hydrate formation were measured in the same manner as in Experimental Example 2, except that the compositions of Examples 1 to 3, Examples 7 to 15 and Comparative Example 2 were used instead of the composition of Example 4. Further, the induction time of the methane hydrate formation was measured using water instead of the composition of Example 4. The results thereof are given in Table 2 below.

TABLE 2

| Composition | Induction time of methane hydrate formation (min) | Composition | Induction time of methane hydrate formation (min) |
|---|---|---|---|
| Example 1 | 17.49 | Example 7 | 75.13 |
| Example 2 | 78.8 | Example 8 | 184.93 |
| Example 3 | 40.41 | Example 9 | 65.8 |
| Example 10 | 51.59 | Example 13 | 124.98 |
| Example 11 | 139.43 | Example 14 | 250.2 |
| Example 12 | 77 | Example 15 | 574.83 |
| Comparative Example 2 | 22.77 | Water | 2.56 |

Figure 3:
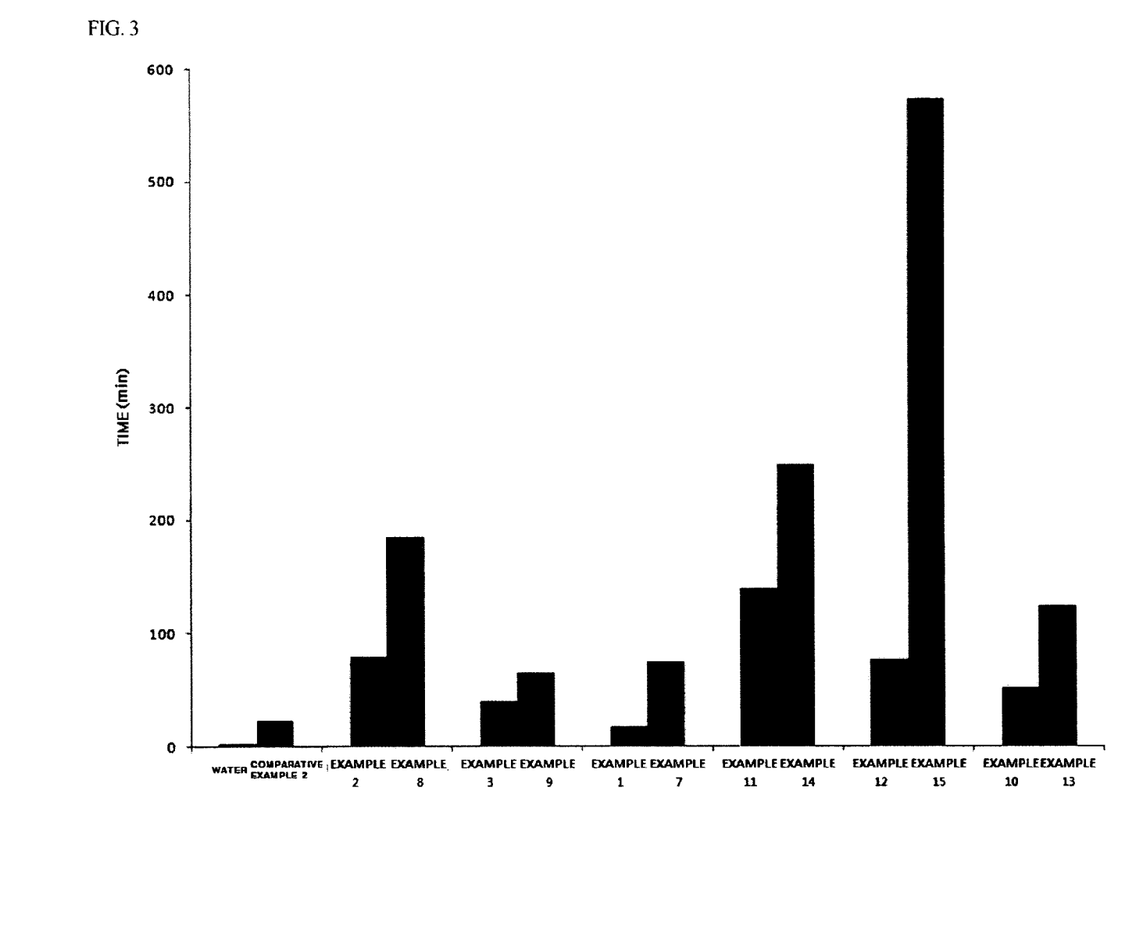
FIG. 3 is a graph showing a delay of a methane hydrate formation according to the composition of the present invention.

As shown in Table 2 and FIG. 3, the compositions of Examples 1 to 3 respectively including the compounds of Preparation Examples 1 to 3 extended the induction time of the methane hydrate formation by 15 minutes or more, compared to water.

Further, the compositions of Examples 7 to 9 respectively including the compounds of Preparation Examples 1 to 3 and polyvinylcaprolactam remarkably extended the induction time of the methane hydrate formation in the same concentration, compared to the compositions of Examples 1 to 3 respectively including the compounds of Preparation Examples 1 to 3 or the composition of Comparative Example 2. Specifically, the compositions of Examples 7 to 9 extended the induction time of the methane hydrate formation by 35~120 minutes in the same concentration, compared to the compositions of Examples 1 to 3.

Further, the compositions of Examples 13 to 15 respectively including 3 wt % of the compounds of Preparation Examples 1 to 3 and polyvinylcaprolactam more remarkably extended the induction time of the methane hydrate formation. That is, the compositions of Examples 13 to 15 extended the induction time of the methane hydrate formation 2~7 times compared to the compositions of Examples 10 to 12.

Accordingly, it can be seen that, when each of the compounds of Preparation Examples 1 to 3 is used together with polyvinylcaprolactam, the formation of methane hydrate can be remarkably delayed compared to when each of the compounds of Preparation Examples 1 to 3 or polyvinylcaprolactam is independently used.

As described above, the composition of the present invention can effectively retard the formation of a gas hydrate. That is, the compound including the ionic liquid compound represented by Chemical Formula 1 and polyvinyl caprolactam can remarkably retard the formation of a gas hydrate compared to when the ionic liquid compound is independently used. Particularly, the composition can effectively retard the formation of a methane hydrate.

Therefore, in the case that work is performed under the condition of a low temperature and a high pressure as that in the sea, when the composition of the present invention is used, the formation of a gas hydrate can be efficiently inhibited in a small quantity.

The foregoing is illustrative of the present invention and is not to be construed as limiting thereof. Although a few example embodiments of the present invention have been described, those skilled in the art will readily appreciate that many modifications are possible in the example embodiments without materially departing from the novel teachings and advantages of this invention. Accordingly, all such modifications are intended to be included within the scope of the present invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The present invention is defined by the following claims, with equivalents of the claims to be included therein.

What is claimed is:

1. A method of inhibiting a gas hydrate formation using polyvinylcaprolactam represented by Chemical Formula 2 below and any one of compounds represented by Chemical Formulae 3 to 5 below:

[Chemical Formula 2]

[Chemical Formula 3]

[Chemical Formula 4]

[Chemical Formula 5]

wherein, in Chemical Formula 2, n is an integer of 5 to 100,
wherein the method comprises introducing the polyvinylcaprolactam represented by Chemical Formula 2 and any one of compounds represented by Chemical Formulae 3 to 5 into a place where the formation of the gas hydrate is to be inhibited.

* * * * *